US012084683B2

United States Patent
Ohashi et al.

(10) Patent No.: US 12,084,683 B2
(45) Date of Patent: Sep. 10, 2024

(54) METHOD FOR INCREASING THE PROPORTION OF DESIRED CELLS FROM INDUCED PLURIPOTENT STEM CELLS

(71) Applicants: TERUMO KABUSHIKI KAISHA, Tokyo (JP); OSAKA UNIVERSITY, Suita (JP)

(72) Inventors: Fumiya Ohashi, Kanagawa (JP); Hiroko Iseoka, Osaka (JP); Yoshiki Sawa, Osaka (JP); Shigeru Miyagawa, Osaka (JP)

(73) Assignees: TERUMO KABUSHIKI KAISHA, Tokyo (JP); OSAKA UNIVERSITY, Osaka (JP)

( * ) Notice: Subject to any disclaimer, the term of this patent is extended or adjusted under 35 U.S.C. 154(b) by 798 days.

(21) Appl. No.: 16/702,755

(22) Filed: Dec. 4, 2019

(65) Prior Publication Data

US 2020/0102541 A1 Apr. 2, 2020

Related U.S. Application Data

(63) Continuation of application No. PCT/JP2018/021475, filed on Jun. 5, 2018.

(30) Foreign Application Priority Data

Jun. 5, 2017 (JP) .................................. 2017-110953

(51) Int. Cl.
| | | |
|---|---|---|
| *C12N 5/077* | (2010.01) | |
| *A61K 35/34* | (2015.01) | |
| *C12N 5/00* | (2006.01) | |
| *C12N 5/071* | (2010.01) | |
| *C12N 5/073* | (2010.01) | |
| *C12N 5/0735* | (2010.01) | |

(52) U.S. Cl.
CPC ............ *C12N 5/0657* (2013.01); *A61K 35/34* (2013.01); *C12N 5/0093* (2013.01); *C12N 5/0602* (2013.01); *C12N 5/0603* (2013.01); *C12N 5/0606* (2013.01); *C12N 2501/115* (2013.01); *C12N 2501/15* (2013.01); *C12N 2501/155* (2013.01); *C12N 2501/16* (2013.01); *C12N 2501/998* (2013.01); *C12N 2506/45* (2013.01)

(58) Field of Classification Search
None
See application file for complete search history.

(56) References Cited

U.S. PATENT DOCUMENTS

| | | | |
|---|---|---|---|
| 2010/0189699 A1 | 7/2010 | Hattori et al. | |
| 2013/0251691 A1 | 9/2013 | Chung et al. | |
| 2015/0353893 A1* | 12/2015 | Burcin | C12N 5/0657 435/377 |
| 2016/0067284 A1 | 3/2016 | Sakamoto et al. | |
| 2017/0335284 A1* | 11/2017 | Masuda | C12N 5/0081 |

FOREIGN PATENT DOCUMENTS

| | | | |
|---|---|---|---|
| CN | 101711277 A | 5/2010 | |
| CN | 106661553 A | 5/2017 | |
| EP | 2 172 542 A1 | 4/2010 | |
| JP | 2015057072 A | 3/2015 | |
| JP | 2015077135 A | 4/2015 | |
| JP | 2016-077159 A | 5/2016 | |
| WO | 2007088874 A1 | 8/2007 | |
| WO | 2015/025958 A1 | 2/2015 | |
| WO | 2015/169762 A1 | 11/2015 | |
| WO | WO-2016072519 A1 * | 5/2016 | ............. A61K 35/33 |

OTHER PUBLICATIONS

Nishikawa et al. The promise of human induced pluripotent stem cells for research and therapy, Nature Reviews Molecular Cell Biology Sep. 2008, 8, 725-729 (Year: 2008).*
Sadelain et al. The Basic Principles of Chimeric Antigen Receptor Design (2013) Cancer Discovery, pp. 388-398. (Year: 2013).*
Park et al. Modification of a Purification and Expansion Method for Human Embryonic Stem Cell-Derived Cardiomyocytes (2013), Cardiology, 124:139-150. (Year: 2013).*
Themeli et al. Generation of tumor-targeted human T lymphocytes from induced pluripotent stem cells for cancer therapy (2013) Nature Biotechnology, 31, pp. 928-933 (Year: 2013).*
Zweigerdt et al. Generation of confluent cardiomyocyte monolayers derived from embryonic stem cells in suspension: a cell source for new therapies and screening strategies (2003) Cytotherapy, 5, pp. 399-413. (Year: 2003).*
Lewandowski et al. Techniques for the induction of human pluripotent stem cell differentiation towards cardiomyocytes (2017) Journal of Tissue Engineering and Regenerative Medicine, 11, pp. 1658-1674. (Year: 2017).*
Matsuura et al. Creation of human cardiac cell sheets using pluripotent stem cells (2012) Biochemical and Biophysical Research Communications, 425, pp. 321-327 (Year: 2012).*
Office Action (Notice of Reasons for Refusal) issued Dec. 17, 2021, by the Japanese Patent Office in corresponding Japanese Patent Application No. 2019-523536 and an English Translation of the Office Action. (10 pages).
Saito et al., "Stem Cell Therapy for Severe Hart Failure," Organ Biology, (month unknown 2009), vol. 16, No. 2, pp. 255-262.
Zweigerdt et al., "Generation of Confluent Cardiomyocyte Monolayers Derived from Embryonic Stem Cells in Suspension: A Cell Source for new Therapies and Screening Strategies," Cytotherapy, (month unknown 2003), vol. 5, No. 5, pp. 399-413.

(Continued)

*Primary Examiner* — Kara D Johnson
*Assistant Examiner* — Maytee Marie Contes De Jesus
(74) *Attorney, Agent, or Firm* — Buchanan Ingersoll & Rooney PC

(57) ABSTRACT

A method for producing a cell culture containing desired cells is provided. The desired cells are induced to be differentiated from pluripotent stem cells. The method includes seeding a cell population by dispersing embryoid bodies obtained by inducing differentiation from the pluripotent stem cells to the desired cells. The embryoid bodies are dispersed at a density reaching confluence or higher.

14 Claims, 4 Drawing Sheets

(56) References Cited

OTHER PUBLICATIONS

Figure 1:
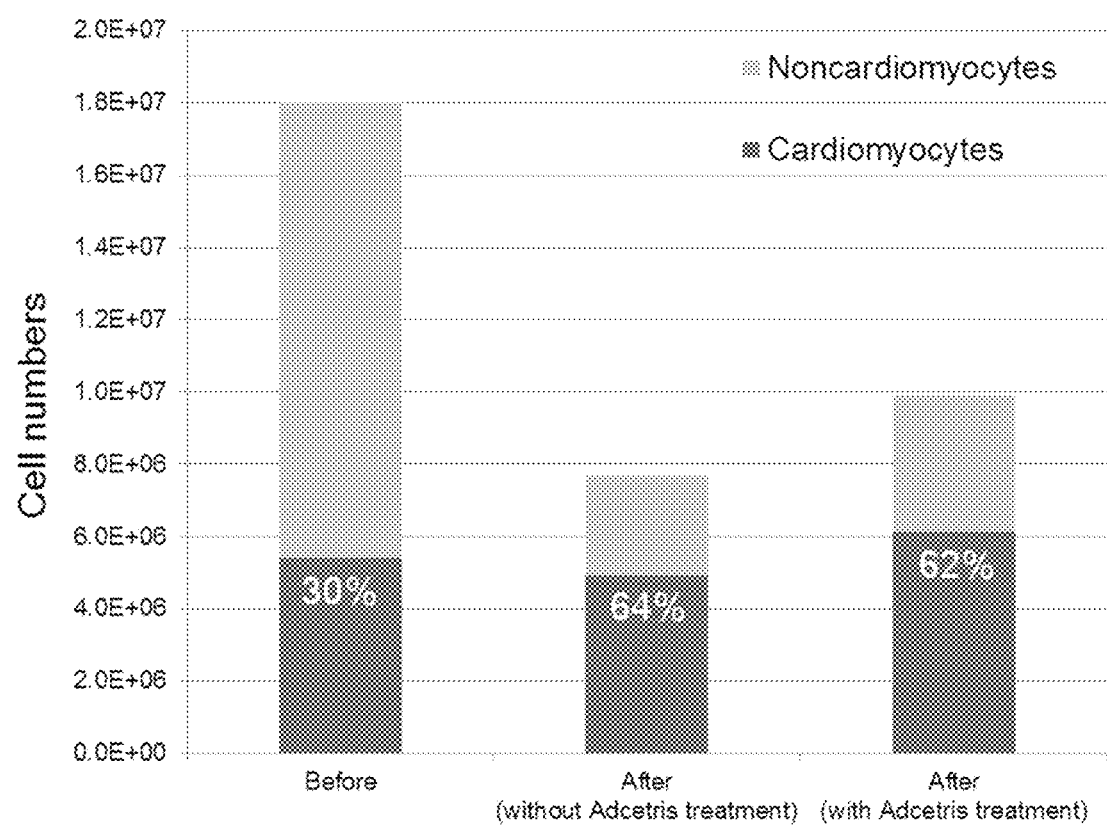

Lian et al., "Directed Cardiomyocyte Differentiation from Human Pluripotent Stem Cells by Modulating Wnt/β-catenin Signaling under fully Defined Conditions," Nature Protocols, (Dec. 20, 2012), vol. 8, No. 1, pp. 162-175.
The extended European Search Report issued on Oct. 15, 2020, by the European Patent Office in corresponding European Patent Application No. 18813547.9-1118. (11 pages).
English Language Translation of Written Opinion of the International Searching Authority (Form PCT/ISA/237) Issued on Aug. 21, 2018, by the Japanese Patent Office in corresponding International Application No. PCT/JP2018/021475. (5 pages).
International Search Report (PCT/ISA/210) issued on Aug. 21, 2018, by the Japanese Patent Office as the International Searching Authority for International Application No. PCT/JP2018/021475.
Chen, "A Journey of Discovery—Pluripotent Stem Cells and Life Sciences Revolution", Military Medical Science Press, (Jun. 2013), pp. 98-100, and an English translation. (7 pages total).
Office Action (The First Office Action) issued Jan. 31, 2023, by the State Intellectual Property Office of People's Republic of China in corresponding Chinese Patent Application No. 201880024869.6 and an English translation of the Office Action. (12 pages).
Office Action (The Second Office Action) issued Aug. 1, 2023, by the State Intellectual Property Office of People's Republic of China in corresponding Chinese Patent Application No. 201880024869.6 and an English translation of the Office Action. (10 pages).
Machine English language translation of the Written Patent Opposition issued on Dec. 26, 2023, in the corresponding Japanese Patent No. 7298844. (25 pages).
Machine English language translation of the Written Submission of Publications issued on Jan. 23, 2024 in the corresponding Japanese Patent Application No. 2023-009177. (15 pages).
Yong Guo et al., "Culturing of Ventricle Cells At High Density and Construction of Engineered Cardiac Cell Sheets Without Scaffold", Int Heart J, Sep. 2009, vol. 50, No. 5, pp. 653-662.
Machine English translation of the Office Action (Notice of Reasons for Refusal) issued on Feb. 29, 2024, in corresponding Japanese Patent Application No. 2023-009177. (4 pages).
Machine English translation of the Opposition Decision issued on Mar. 5, 2024, in the corresponding Japanese Patent No. 7298844. (21 pages).

\* cited by examiner

METHOD FOR INCREASING THE PROPORTION OF DESIRED CELLS FROM INDUCED PLURIPOTENT STEM CELLS

CROSS-REFERENCES TO RELATED APPLICATIONS

This application is a continuation of International Application No. PCT/JP2018/021475 filed on Jun. 5, 2018, which claims priority to Japanese Application No. 2017-110953 filed on Jun. 5, 2017, the entire content of both of which is incorporated herein by reference.

TECHNICAL FIELD

The present invention generally relates to a method for producing a cell culture containing desired cells that is induced to be differentiated from pluripotent stem cells, a method for producing a sheet-shaped cell culture containing the cell culture, a composition, a graft and a medical product including the cell culture or the sheet-shaped cell culture, a method for treating a disease using the desired cell culture or the sheet-shaped cell culture, and a kit for producing the cell culture or the sheet-shaped cell culture.

BACKGROUND DISCUSSION

In recent years, attempts have been made to implant various cells for repairing damaged tissues and the like. Recently attracting attention as a source of such cells are cells derived from pluripotent stem cells such as embryonic stem cells (ES cells) and induced pluripotent stem cells (iPS cells). However, when attempting to induce differentiation of pluripotent stem cells into desired cells, it is technically difficult to differentiate all cells into desired cells, and in a cell population induced to be differentiated from pluripotent stem cells, not only desired cells but also other types of cells are included.

For example, when the desired cells are cardiomyocytes, a method of increasing the ratio of the desired cell in the cell population, a method of culturing the desired cells under a specific nutrient condition (Park S. et al., Cardiology 2013; 124: 139-150 and Tohyama S. et al., Cell Stem Cell 12, 127-137, Jan. 3, 2013, and International Patent Application Publication No. 2007/088874) or a method of purifying the desired cells with magnetic beads (Dubois, N. C. et al. Nat. Biotechnol. 29, 1011-8 (2011)) is known.

SUMMARY

An object of the present invention is to provide a method for producing a cell culture containing desired cells induced to be differentiated from pluripotent stem cells, a method for producing a sheet-shaped cell culture containing the cell culture, a composition, a graft and a medical product including the cell culture or the sheet-shaped cell culture, a method of treating a disease using the desired cell culture or the sheet-shaped cell culture, and a kit for producing the cell culture or the sheet-shaped cell culture.

When cells induced to be differentiated from pluripotent stem cells are used for transplantation, it is essential to efficiently obtain a cell population containing a high proportion of desired cells. Although conventional methods for increasing the proportion of desired cells increase the proportion of desired cells, it may not be an efficient method since the recovery rate of cells is low.

As a result of intensive research on a method for efficiently preparing cardiomyocytes from pluripotent stem cells, the inventors surprisingly discovered that seeding a cell population wherein embryoid bodies are dispersed at a density which reaches confluence or higher results in the content of cardiomyocytes higher than the cell population before seeding, and the content of other cells lower than the cell population before seeding. As a result of continuing research based on such knowledge, the inventors arrived at the following aspects and embodiments.

An aspect is directed to a method for producing a cell culture containing desired cells. The desired cells are induced to be differentiated from pluripotent stem cells. The method includes seeding a cell population by dispersing embryoid bodies obtained by inducing differentiation from the pluripotent stem cells to the desired cells. The embryoid bodies are dispersed at a density reaching confluence or higher.

In one embodiment, the density reaching confluence is a density at which cell proliferation is substantially stopped by contact inhibition.

In another embodiment, the cell culture produces the desired cells at a higher proportion in the cell population than produced without seeding.

In another embodiment, the cell culture produces a cell group having a high proliferation rate relative to the desired cells at a lower proportion in the cell population than produced without seeding.

In another embodiment, the method further includes removal of cells having tumorigenicity.

In another embodiment, the removal of cells having tumorigenicity includes treating with Brentuximab/Vedotin.

In another embodiment, the pluripotent stem cells are iPS cells.

In another embodiment, the pluripotent stem cells are human cells.

In another embodiment, the desired cells are cells for application to a subject in need thereof.

In another embodiment, the desired cells are applied to a heart, a lung, a liver, a pancreas, a kidney, a large intestine, a small intestine, a spinal cord, a central nervous system, a bone, an eye, skin, a blood vessel or blood.

In another embodiment, the desired cells are mesenchymal stem cells, skeletal myoblasts, multipotent cardiac progenitor cells, unipotent cardiac progenitor cells, cardiomyocytes, skeletal muscle cells, smooth muscle cells, hemangioblasts, epithelial cells, endothelial cells, lung cells, liver cells, pancreatic cells, renal cells, adrenal cells, intestinal epithelial cells, neural stem cells, bone marrow stromal cells, neural cells, corneal epithelial cells, corneal endothelial cells, retinal pigment epithelial cells, T cells, NK cells, NKT cells, dendritic cells, or blood cells.

In another embodiment, the desired cells are cardiomyocytes.

In another embodiment, a cell culture having a troponin positive rate of 50% to 90% is obtained.

In another embodiment, a cell culture having a Lin28 positive rate of 0.30% or less is obtained.

Another aspect is directed to a method for producing a sheet-shaped cell culture. The method includes sheet-forming of the cell culture obtained by the foregoing method.

Another aspect is directed to a method for increasing the proportion of desired cells in a cell culture. The method includes seeding the cell culture by dispersing embryoid bodies obtained by inducing differentiation from the pluripotent stem cells to the desired cells, and allowing the embryoid bodies to reach a density reaching confluence or higher.

Another aspect is directed to a cardiomyocyte prepared by a method that includes the steps of seeding a cell culture by dispersing embryoid bodies obtained by inducing differentiation from the pluripotent stem cells to cardiomyocytes, and allowing the embryoid bodies to reach a density reaching confluence or higher.

The method provides the advantage that the proportion of desired cells in the cell culture may increase, in the case where the desired cells are cells having a relatively low proliferation rate among the desired cells and other cells contained in a cell population in which embryoid bodies obtained by inducing differentiation from pluripotent stem cells to the desired cells are dispersed, by seeding the cell population at a high density, for example, a density reaching confluence or higher, to enable the content of the desired cells to be increased compared to the cell population before seeding and enable the content of cells other than the desired cells, which have a high proliferation rate relative to the desired cells, to be decreased compared to the cell population before seeding. Furthermore, according to this method, the proportion of recoverable viable cells is higher than in the prior art, so the amount of final recoverable desired cells is dramatically increased. In addition, the method may further include removal of cells having tumorigenicity to obtain a cell culture with a reduced risk of tumorigenesis. The cell culture of this method is highly compatible to the conventional method for producing a sheet-shaped cell culture, with a minimal labor and cost, and thus this method may be widely used for producing a sheet-shaped cell culture. It is possible to produce a sheet-shaped cell culture by optionally subjecting the cell culture obtained by this method to freezing and thawing operations and then forming it into a sheet.

BRIEF DESCRIPTION OF THE DRAWING FIGURES

FIG. 1 is a graph showing results in a high density culture method. From the left to the right side, before seeding, after seeding (without Adcetris® treatment), and after seeding (with Adcetris® treatment) are shown. The vertical axis represents the number of cells, "cardiomyocytes" represents cardiomyocyte cells, and "noncardiomyocytes" represents non cardiomyocyte cells.

Figure 2:
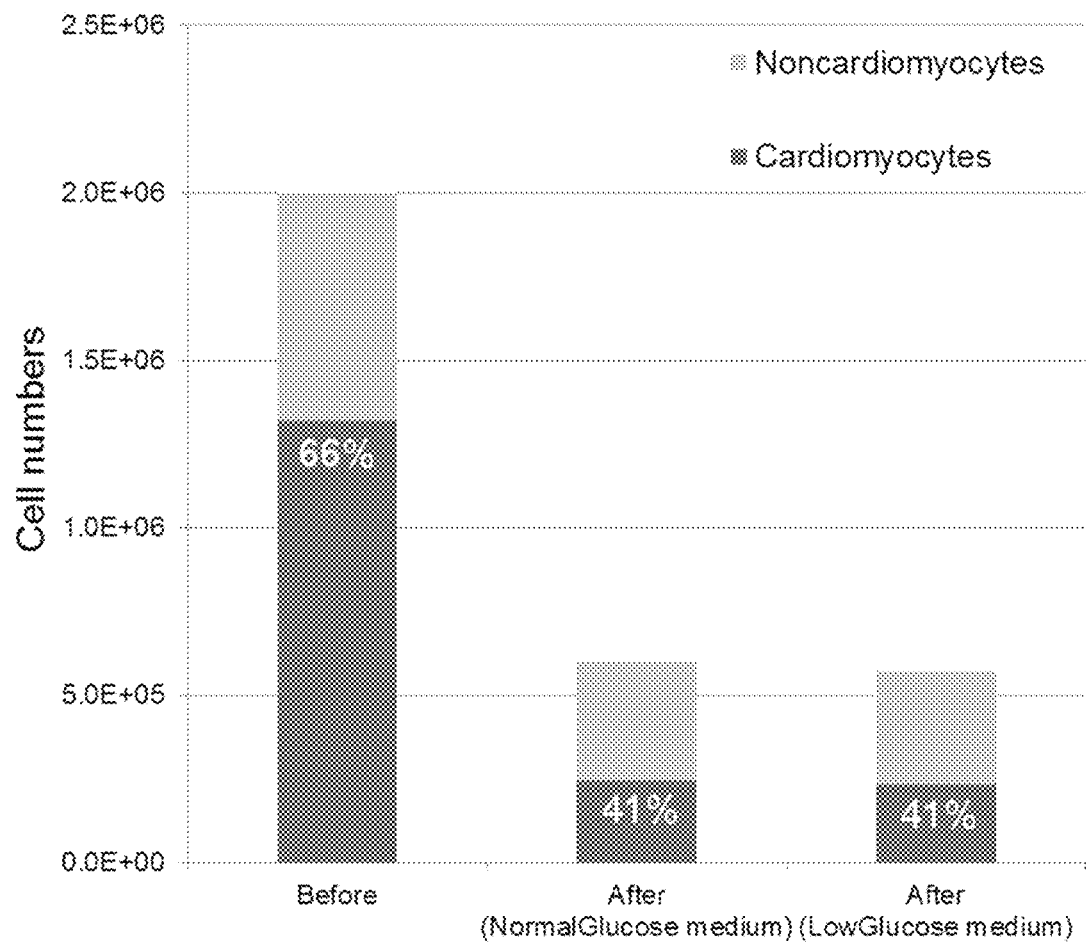

FIG. 2 is a graph showing results in a low density culture method. From the left to the right side, before seeding, after seeding (Normal Glucose medium) and after seeding (Low Glucose medium) are shown. The vertical axis represents the number of cells, "cardiomyocytes" represents cardiomyocyte cells, and "noncardiomyocytes" represents non cardiomyocyte cells.

Figure 3:
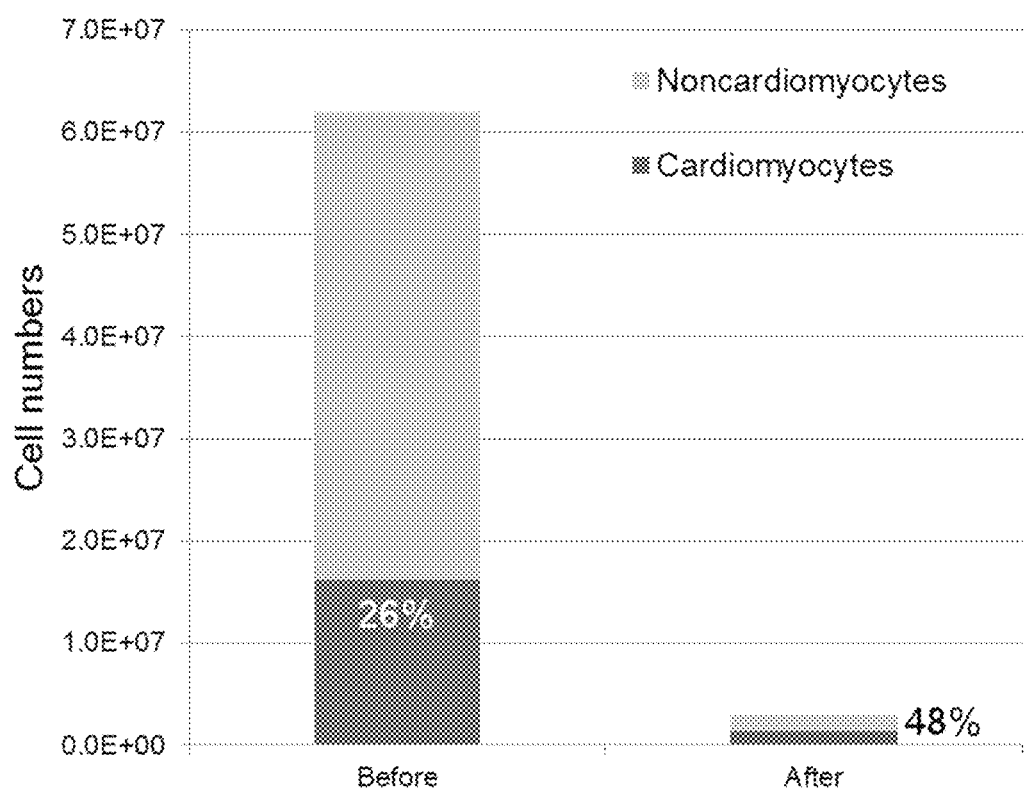

FIG. 3 is a graph showing results in a reaggregation method and No Glucose purification method. From the left to the right side, before seeding and after seeding are shown. The vertical axis represents the number of cells, "cardiomyocytes" represents cardiomyocyte cells, and "noncardiomyocytes" represents non cardiomyocyte cells.

Figure 4:
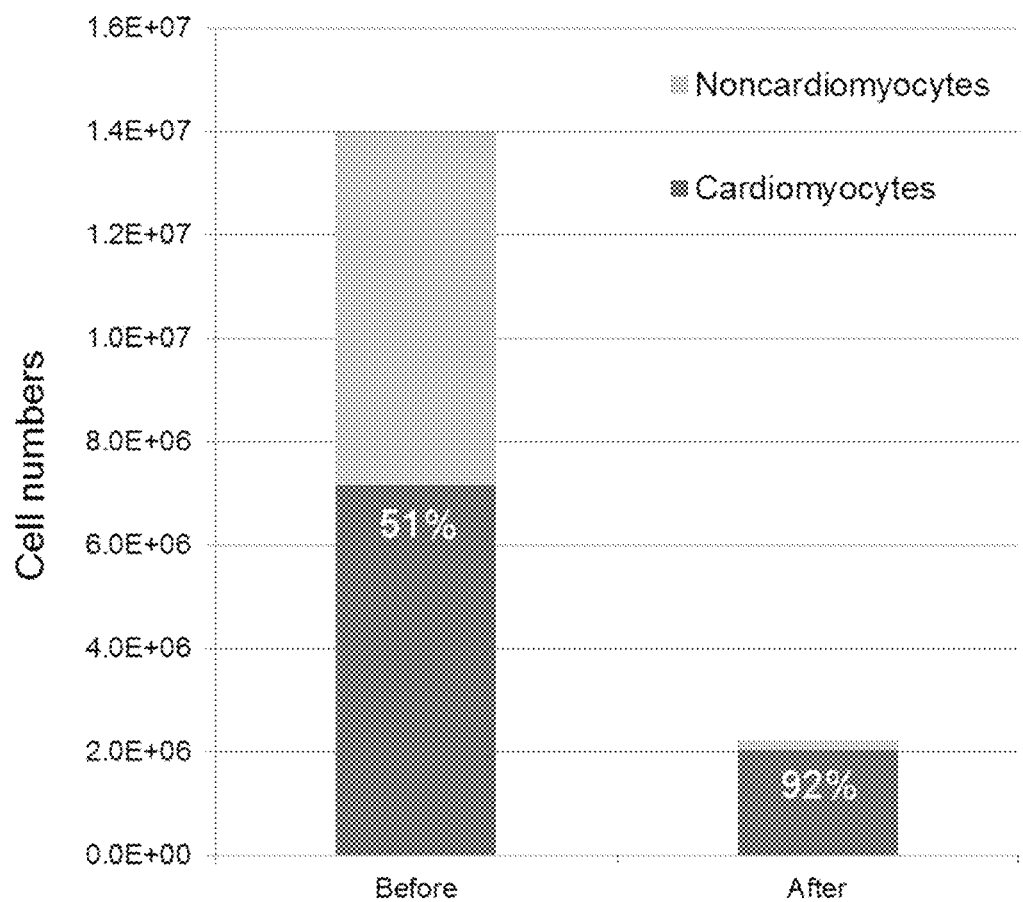

FIG. 4 is a graph showing results in a method using MACS. From the left to right side, before purification and after purification are shown. The vertical axis represents the number of cells, "cardiomyocytes" represents cardiomyocyte cells, and "noncardiomyocytes" represents non cardiomyocyte cells.

DETAILED DESCRIPTION

Set forth below with reference to the accompanying drawings is a detailed description of embodiments of a method for producing a cell culture containing desired cells that is induced to be differentiated from pluripotent stem cells, a method for producing a sheet-shaped cell culture containing the cell culture, a composition, a graft and a medical product including the cell culture or the sheet-shaped cell culture, a method for treating a disease using the desired cell culture or the sheet-shaped cell culture, and a kit for producing the cell culture or the sheet-shaped cell culture representing examples of the inventive methods, composition, graft, medical product and kit disclosed here.

Unless indicated otherwise herein, all technical and scientific terms have the same meanings as commonly understood by those skilled in the art. All patents, patent applications and other publications and information referenced herein are hereby incorporated by reference in their entirety. In addition, in the case of conflict between the publication referred to in the present specification and the description in the present specification, the description in the present specification shall prevail.

In the present disclosure, the term "pluripotent stem cell" is a term well known in the art and means a cell having the ability to differentiate into cells of all lineages belonging to tridermal lineages, i.e., endoderm, mesoderm and ectoderm. Non-limiting examples of pluripotent stem cells include, for example, embryonic stem cells (ES cells), nuclear transplanted embryonic stem cells (ntES cells), induced pluripotent stem cells (iPS cells), and the like. Usually, when pluripotent stem cells are induced to be differentiated into specific cells, first, pluripotent stem cells are suspended and cultured to form aggregates of any of the above three germ layers and then cells forming the aggregates are induced to be differentiated into specific cells of interest. In the present disclosure, "embryoid body" means an aggregate of such cells.

In the present disclosure, "cells having a relatively high proliferation rate" mean cells that show a greater increase per unit time when the increase in the number of cells per unit time in a given environment of a certain cell is compared to the increase in the number of cells per unit time in the given environment of another cell, for example. Also, conversely, "cells having a relatively low proliferation rate" mean cells that do not show a greater increase per unit time when the increase in the number of cells per unit time in a given environment of a certain cell is compared to the increase in the number of cells per unit time in the given environment of another cell, for example. Whether cells are "cells having a relatively high proliferation rate" or "cells having a relatively low proliferation rate," compared to other cells can be determined by methods known to one of ordinary skill in the art, and may be determined by comparing the doubling time, the doubling number, the change in weight with time, or the change in the occupied area of the culture vessel with time of cells, and the like, for example.

In the present disclosure, "having a relatively high proliferation rate" means that for example, the increase in the number of cells per unit time in a predetermined environment of a certain cell, doubling time, doubling number, the change of weight with time, or the change in the occupied area of the culture vessel with time of the cells is 10% or more, 20% or more, 30% or more, 40% or more, 50% or more, 60% or more, 70% or more, 80% or more, 90% or more, 100% or more, 200% or more, 300% or more, 400% or more, 500% or more, 600% or more, 700% or more, 800% or more, 900% or more, or 1000% or more, compared to the values in other cells.

Also, conversely, in the present disclosure, "having a relatively low proliferation rate" means that for example, the increase in the number of cells per unit time in a given environment of a certain cell, doubling time, doubling number, the change of weight with time, the change of the occupied area in the culture vessel of cells is 10% or less, 20% or less, 30% or less, 40% or less, 50% or less, 60% or less, 70% or less, 80% or less, 90% or less, 100% or less, 200% or less, 300% or less, 400% or less, 500% or less, 600% or less, 700% or less, 800% or less, 900% or less, or 1000% or less, compared to the values in other cells.

In the present disclosure, the "density reaching confluence" refers to a density that is assumed to cause cells to cover the adhesion surface of the culture vessel when seeded. For example, it is a density at which cells are expected to contact each other when seeded, a density at which contact inhibition occurs, or a density at which the growth of the cells is substantially stopped by the contact inhibition.

In the present disclosure, the "cell having tumorigenicity" means a cell that is at risk to be tumorigenic after transplantation. Non-limiting examples of cells having tumorigenicity include cells that still have pluripotency (undifferentiated cells) even after differentiation-induced treatment and cells wherein genomic abnormalities occur, and the cells are typically undifferentiated.

In the present disclosure, "undifferentiated cells" are cells that still have pluripotency for differentiation even after differentiation-induced treatment. Typically, it refers to cells that express markers characteristic of the undifferentiated state, such as Lin28, Tra-1-60, and the like.

In the present disclosure, the term "subject" means any living individual, preferably an animal, more preferably a mammal, still more preferably a human. In the present invention, the subject may be healthy or may be suffering from any disease, but when treatment of a disease associated with tissue abnormality is intended, the subject typically means a subject who is suffering from or at risk of suffering from the disease.

In the present disclosure, the term "mesenchymal stem cells" is a term well known in the art, and means cells which exist in mesenchymal tissue and have the ability to differentiate into cells belonging to mesenchymal tissue.

In the present disclosure, "multipotent cardiac progenitor cells" mean cardiac progenitor cells having the ability to differentiate into multiple mature cells such as cardiomyocyte cells, smooth muscle cells, and vascular endothelial cells, and include, for example, the multipotent cardiac progenitor described in Ishida H. et al., Cell Reports (2016) Jul. 26; 16 (4): 1026-38. In the present disclosure, the term "unipotent cardiac progenitor cells" means cardiac progenitor cells that differentiate only into cardiomyocytes, and include, for example, the Cardiomyocyte precursor described in Ishida H. et al., Cell Reports (2016) Jul. 26; 16 (4): 1026-38, and the like.

In the present disclosure, "cardiomyocytes" mean cells having characteristics of cardiomyocyte. Characteristics of cardiomyocyte include, but are not limited to, for example, the expression of cardiomyocyte markers, the presence of an autonomous beat, and the like. Non-limiting examples of cardiomyocyte markers include, for example, c-TNT (cardiac troponin T), CD172a (also known as SIRPA or SHPS-1), KDR (also known as CD309, FLK1 or VEGFR2), PDGFRA, EMILIN2, VCAM, etc. In one embodiment, pluripotent stem cell-derived cardiomyocytes are c-TNT positive and/or CD172a positive.

In the present disclosure, "sheet-shaped cell culture" refers to cells which are linked to each other to form a sheet. The cells may be linked to each other directly (including via cell components such as adhesion molecules) and/or via an intermediary substance. The intermediary substance is not particularly limited as long as it is a substance capable of at least physically (mechanically) connecting cells to each other, and examples thereof include an extracellular matrix and the like. The intermediary substance is preferably originated from a cell, in particular originated from the cells constituting the cell culture. The cells are at least physically (mechanically) linked, but may be further functionally linked, for example, chemically or electrically. The sheet-shaped cell culture may be composed of one cell layer (monolayer), and may be composed of two or more cell layers (laminate (multilayer), for example, two layers, three layers, four layers, five layers, six layers, etc.).

One aspect of the disclosure involves a method for producing a cell culture containing desired cells induced to be differentiated from pluripotent stem cells, the method including seeding, at a density reaching confluence or higher, a cell population, in which embryoid bodies obtained by inducing differentiation from the pluripotent stem cells to the desired cells are dispersed and the desired cells and cells having a high proliferation rate relative to the desired cells are obtained. The cell culture obtained by the method contains the desired cells at a higher proportion than the cell population before seeding, and contains a cell group having a high proliferation rate relative to the desired cells at a lower proportion than the cell population before seeding.

While not wishing to be bound by a particular theory, it is considered that by virtue of seeding cells at a density that reaches confluence, while the growth of a cell group that has a high proliferation rate relative to the desired cells may be suppressed by contact inhibition, inter-cellular communication of the desired cells is better when seeded at a higher density than when seeded at a low density, and therefore the desired cells are consequently obtained at a proportion higher than the proportion in the cell population before seeding, and a cell culture, which contains a cell group having a high proliferation rate relative to the desired cells at a proportion lower than the proportion in the cell population before seeding, may be obtained.

In one aspect, differentiation of pluripotent stem cells into desired cells may be induced using methods known to one of ordinary skill in the art. For example, for induction of differentiation of pluripotent stem cells into cardiomyocytes, reference may be made to Miki K. et al., Cell Stem Cell. 2015 Jun. 4; 16 (6): 699-711, and International Application Publication No. 2014/185358. Specifically, by sequentially causing mesodermal inducers (e.g., activin A, BMP4, bFGF, VEGF, SCF, etc.), cardiac specification factors (e.g., VEGF, DKK1, Wnt signal inhibitors (e.g., IWR-1, IWP-2, IWP-3, IWP-4, etc.), BMP signal inhibitors (e.g., NOGGIN, etc.), TGFβ/activin/NODAL signal inhibitors (e.g., SB431542, etc.), retinoic acid signal inhibitors, etc.), and cardiac differentiation factors (e.g., VEGF, bFGF, DKK1, etc.) to act, the induction efficiency may be enhanced. In one embodiment, cardiomyocyte induction treatment from pluripotent stem cells is carried out by sequentially causing (1) a combination of BMP4, bFGF and activin A; (2) a combination of VEGF and IWP-3; and (3) a combination of VEGF and bFGF to act on embryoid bodies formed by the action of BMP4.

A method of obtaining cardiomyocytes from human iPS cells includes, for example, the following steps:
(1) maintaining and culturing an established human iPS cells in a feeder cell-free medium (feeder free method);
(2) forming embryoid bodies from the obtained iPS cells;
(3) culturing the obtained embryoid bodies in a culture solution containing activin A, bone morphogenetic protein (BMP) 4 and basic fibroblast growth factor (bFGF);
(4) culturing the obtained embryoid bodies in a culture solution containing a Wnt inhibitor, a BMP4 inhibitor and a TGFβ inhibitor; and
(5) culturing the obtained embryoid bodies in a culture solution containing VEGF and bFGF.

In step (1), for example, as described in International Application Publication No. 2017/038562 A, using StemFit® AK03 (Ajinomoto Co., Inc.) as a culture medium, iPS cells can be cultured and adapted on iMatrix™ 511 (Nippi, Incorporated) to be maintained and cultured. In addition, as described in, for example, Nakagawa M., et al. A novel efficient feeder-free culture system for the derivation of human induced pluripotent stem cells. Sci Rep. 2014; 4:3594, passage of iPS cells may be performed every 7 to 8 days in a single cell state using TrypLE® Select (Thermo Fisher Scientific K.K.). After the above steps (1) to (5), the step (6) of optionally purifying the obtained cardiomyocytes may be selectively performed. Purification of cardiomyocytes includes a method of reducing cells other than cardiomyocytes using a glucose free medium, a method of reducing undifferentiated cells using heat treatment as described in International Application Publication No. 2017/038562, and the like.

In the present disclosure, "dispersing embryoid bodies" means making embryoid bodies (aggregates) being finer structures. Examples of finer structures include, for example, single cells and cell clusters. The size of the finer structure may be any size smaller than the original embryoid body, for example, a diameter of 100 μm or less, a diameter of 90 μm or less, a diameter of 80 μm or less, a diameter of 70 μm or less, a diameter of 60 μm or less, a diameter of 50 μm or less, a diameter of 40 μm or less, a diameter of 30 μm or less, a diameter of 20 μm or less, or a diameter of 10 μm or less.

In the present disclosure, the dispersion of embryoid bodies may be performed using techniques known to one of ordinary skill in the art. Such techniques include, but are not limited to, chemical methods using, for example, trypsin/EDTA, pronase, dispase, collagenase, CTK (REPROCELL), TrypLE® Select (Thermo Fisher Scientific K.K.), etc., as a cell dispersant, and physical methods such as pipetting, and the like.

In the present disclosure, the density reaching confluence is a density at which the cells are expected to cover the entire adhesion surface of the culture vessel when cells are seeded as described above, for example, a density at which cells are expected to be brought into contact with each other when seeded, a density at which contact inhibition occurs, or a density at which cell growth is substantially stopped by contact inhibition, and can be calculated by those skilled in the art from the size of the desired cell and the area of the adhesion surface of the culture vessel. Therefore, those skilled in the art may also determine the optimal seeding density as appropriate. The upper limit of the seeding density is not particularly limited, but if the density is excessively high, many cells die and it becomes inefficient. In one embodiment, the seeding density is, for example, about $1.0 \times 10^5$ cells/cm$^2$ to about $1.0 \times 10^8$ cells/cm$^2$, about $5.0 \times 10^5$ cells/cm$^2$ to about $5.0 \times 10^7$ cells/cm$^2$, or about $1.0 \times 10^6$ cells/cm$^2$ to about $1.0 \times 10^7$ cells/cm$^2$. In another embodiment, the seeding density is about $1.0 \times 10^5$ cells/cm$^2$ or more, about $2.0 \times 10^5$ cells/cm$^2$ or more, about $3.0 \times 10^5$ cells/cm$^2$ or more, about $4.0 \times 10^5$ cells/cm$^2$ or more, about $5.0 \times 10^5$ cells/cm$^2$ or more, about $6.0 \times 10^5$ cells/cm$^2$ or more, about $7.0 \times 10^5$ cells/cm$^2$ or more, about $8.0 \times 10^5$ cells/cm$^2$ or more, about $9.0 \times 10^5$ cells/cm$^2$ or more, about $1.0 \times 10^6$ cells/cm$^2$ or more, about $2.0 \times 10^6$ cells/cm$^2$ or more, about $3.0 \times 10^6$ cells/cm$^2$ or more, about $4.0 \times 10^6$ cells/cm$^2$ or more, about $5.0 \times 10^6$ cells/cm$^2$ or more, about $6.0 \times 10^6$ cells/cm$^2$ or more, about $7.0 \times 10^6$ cells/cm$^2$ or more, about $8.0 \times 10^6$ cells/cm$^2$ or more, about $9.0 \times 10^6$ cells/cm$^2$ or more, about $1.0 \times 10^7$ cells/cm$^2$ or more, about $2.0 \times 10^7$ cells/cm$^2$ or more, about $3.0 \times 10^7$ cells/cm$^2$ or more, about $4.0 \times 10^7$ cells/cm$^2$ or more, about $5.0 \times 10^7$ cells/cm$^2$ or more, about $6.0 \times 10^7$ cells/cm$^2$ or more, about $7.0 \times 10^7$ cells/cm$^2$ or more, about $8.0 \times 10^7$ cells/cm$^2$ or more, about $9.0 \times 10^7$ cells/cm$^2$ or more, or about $1.0 \times 10^8$ cells/cm$^2$ or more. The above range may include both the upper limit and the lower limit, or any one of them, as long as the lower limit is $1.0 \times 10^5$ cells/cm$^2$ or more.

In another embodiment, the proportion of desired cells in the obtained cell culture is a proportion higher than the proportion of desired cells in the cell population before seeding. The proportion of desired cells in the cell culture may be, for example, more than about 50%, more than about 51%, more than about 52%, more than about 53%, more than about 54%, more than about 55%, more than about 56%, more than about 57%, more than about 58%, more than about 59%, more than about 60%, more than about 61%, more than about 62%, more than about 63%, more than about 64%, more than about 65%, more than about 66%, more than about 67%, more than about 68%, more than about 69%, more than about 70%, more than about 71%, more than about 72%, more than about 73%, more than about 74%, more than about 75%, more than about 76%, more than about 77%, more than about 78%, more than about 79%, more than about 80%, more than about 81%, more than about 82%, more than about 83%, more than about 84%, more than about 85%, more than about 86%, more than about 87%, more than about 88%, more than about 89%, more than about 90%, more than about 91%, more than about 92%, more than about 93%, more than about 94%, more than about 95%, more than about 96%, more than about 97%, more than about 98%, or more than about 99%.

In another embodiment, in the case where the desired cell is a cardiomyocyte, the proportion of cardiomyocytes in the obtained cell culture is higher than the proportion of cardiomyocytes in the cell population before seeding. The proportion of cardiomyocytes in the cell culture may be, for example, more than about 50%, more than about 51%, more than about 52%, more than about 53%, more than about 54%, more than about 55%, more than about 56%, more than about 57%, more than about 58%, more than about 59%, more than about 60%, more than about 61%, more than about 62%, more than about 63%, more than about 64%, more than about 65%, more than about 66%, more than about 67%, more than about 68%, more than about 69%, more than about 70%, more than about 71%, more than about 72%, more than about 73%, more than about 74%, more than about 75%, more than about 76%, more than about 77%, more than about 78%, more than about 79%, more than about 80%, more than about 81%, more than about 82%, more than about 83%, more than about 84%, more than about 85%, more than about 86%, more than about 87%, more than about 88%, more than about 89%, more than about 90%, more than about 91%, more than about 92%, more than about 93%, more than about 94%, more than about 95%, more than about 96%, more than about 97%, more than about 98%, more than about 99%.

The cell culture obtained by the method of the present embodiment contains a large number of cardiomyocytes, i.e., troponin (c-TNT) positive cells. The troponin positive rate of the cells in the obtained cell culture is not limited to these, but may be, for example, 50% or more, 51% or more, 52% or more, 53% or more, 54% or more, 55% or more, 56% or more, 57% or more, 58% or more, 59% or more, 60% or more, 61% or more, 62% or more, 63% or more, 64% or more, 65% or more, 66% or more, 67% or more, 68% or more, 69% or more, 70% or more, 71% or more, 72% or more, 73% or more, 74% or more, or 75% or more.

Moreover, the troponin positive rate of the cells in the obtained cell culture is not limited to these, but may be, for example, 99% or less, 98% or less, 97% or less, 96% or less, 95% or less, 94% or less, 93% or less, 92% or less, 91% or less, 90% or less, 89% or less, 88% or less, 87% or less, 86% or less, 85% or less, 84% or less, 83% or less, 82% or less, 81% or less, or 80% or less.

Therefore, the range of troponin positive rate of cells in the obtained cell culture may be any combination of the above upper limit values and the lower limit values. In a preferred embodiment, the troponin positive rate of the obtained cell culture may be, for example, 50% to 90%, 55% to 90%, 60% to 90%, 50% to 85%, 55% to 85%, 60% to 85%, 50% to 80%, 55% to 80%, 60% to 80%, 50% to 75%, 55% to 75%, 60% to 75%, 50% to 70%, 55% to 70% 60% to 70%, or 60% to 65%.

In another embodiment, the troponin positive rate of the obtained cell culture may be, for example, 50% to 90%, 55% to 90%, 60% to 90%, 50% to 85%, 55% to 85%, 60% to 85%, 50% to 80%, 55% to 80%, 60% to 80%, 50% to 75%, 55% to 75%, 60% to 75%, 50% to 70%, 55% to 70%, 60% to 70%, 60% to 65%, etc., and the positive rate of Lin28 is, for example, 0.35% or less, 0.30% or less, 0.25% or less, 0.20% or less, 0.15% or less, 0.10% or less, or 0.05% or less.

In another embodiment, the troponin positive rate of the cells in the obtained cell culture is 50% to 90%, and the positive rate of Lin28 is 0.30% or less.

In another embodiment, the troponin positive rate of cells in the obtained cell culture is 60% to 80%, and the positive rate of Lin28 is 0.30% to 0.20%.

In another embodiment, the proportion of the cell group having a high proliferation rate relative to the desired cells in the cell culture is a proportion lower than the proportion of the same cell group in the cell population before seeding. In an embodiment, the proportion thereof may be, for example, less than about 50%, less than about 49%, less than about 48%, less than about 47%, less than about 46%, less than about 45%, less than about 44%, less than about 43%, less than about 42%, less than about 41%, less than about 40%, less than about 39%, less than about 38%, less than about 37%, less than about 36%, less than about 35%, less than about 34%, less than about 33%, less than about 32%, less than about 31%, less than about 30%, less than about 29%, less than about 28%, less than about 27%, less than about 26%, less than about 25%, less than about 24%, less than about 23%, less than about 22%, less than about 21%, less than about 20%, less than about 19%, less than about 18%, less than about 17%, less than about 16%, less than about 15%, less than about 14%, less than about 13%, less than about 12%, less than about 11%, less than about 10%, less than about 9%, less than about 8%, less than about 7%, less than about 6%, less than about 5%, less than about 4%, less than about 3%, less than about 2%, or less than about 1%.

In another embodiment, the method further includes removal of cells having tumorigenicity. Removal of cells having tumorigenicity can be performed using any techniques known to one of ordinary skill in the art. Non-limiting examples of such techniques include various separation methods using markers specific to cells having tumorigenicity (e.g., cell surface markers, etc.), such as magnetic cell separation (MACS), flow cytometry, an affinity separation method, a method of allowing a selection marker (e.g., antibiotic resistance gene, etc.) to express with a specific promoter, a method of culturing in a medium from which nutrient sources (such as methionine) necessary for survival of cells having tumorigenicity is removed to eliminate undifferentiated cells, a method of treating with a drug targeting the surface antigen of cells having tumorigenicity, and as a known method of removing undifferentiated cells, a method described in International Application Publication No. 2014/126146 and International Application Publication No. 2012/056997, a method described in International Application Publication No. 2012/147992, a method described in International Application Publication No. 2012/133674, a method described in International Application Publication No. 2012/012803 (JP 2013-535194), a method described in International Application Publication No. 2012/078153 (Japanese Patent Application No. 2014-501518), a method described in Japanese Patent Application No. 2013-143968 A and Tohyama S. et al., Cell Stem Cell Vol. 12 Jan. 2013, Page 127-137, a method described in Lee M O et al., PNAS 2013 Aug. 27; 110(35): E3281-90, a method described in International Application Publication No. 2016/072519, a method described in International Application Publication No. 2013/100080, a method described in JP 2016-093178, a method using heat treatment described in International Application Publication No. 2017/038526, and the like. In a preferred embodiment, removal of cells having tumorigenicity is carried out using Brentuximab-Vedotin.

Brentuximab-Vedotin is an antibody-drug complex in which an antibody targeting CD30 antigen and a low molecular weight drug (monomethyl auristatin E: MMAE) having microtubule inhibitory activity are combined, and is commercially available under the brand name of ADCETRIS®. It is a therapeutic agent for relapsed/refractory CD30 positive Hodgkin's lymphoma, etc., and can selectively act on cells expressing CD30 antigen. Since CD30 antigen is highly expressed in undifferentiated cells, undifferentiated cells may be removed by Brentuximab-Vedotin (International Application Publication No. 2016/072519). As a specific operation, it is carried out by adding Brentuximab-Vedotin to the culture medium and incubating it.

In one embodiment, when the cells having tumorigenicity were removed, the positive rate of Lin28 of the cells in the obtained cell culture may be, for example, 0.35% or less, 0.30% or less, 0.25% or less, 0.20% or less, 0.15% or less, 0.10% or less, 0.05% or less, and the like.

In another embodiment, the range of the positive rate of Lin28 of cells in the obtained cell culture may be, for example, 0.35% to 0.10%, 0.30% to 0.20%, 0.25% to 0.20%, and the like.

In another embodiment, pluripotent stem cells are, for example, embryonic stem cells (ES cells), nuclear transplanted embryonic stem cells (ntES cells), induced pluripotent stem cells (iPS cells), and the like. Preferably, the pluripotent stem cells are iPS cells.

In another embodiment, pluripotent stem cells may be derived from any organism. Such organisms include, but are not limited to, humans, non-human primates, dogs, cats, pigs, horses, goats, sheep, rodents (e.g., mice, rats, hamsters, guinea pigs, etc.), rabbits, etc. Preferably, the pluripotent stem cells are human cells.

In another embodiment, the desired cell is a cell for application to a subject in need thereof. In the case where the subject is a specific animal, for example, a series of steps in the method of producing a cell culture is performed in an environment free of heterologous components. In the case where the subject is a human, a series of steps in the method of producing a cell culture is performed, for example, in an environment not containing non-human derived components, and specifically, for example, xeno-free reagents are used and culture is carried out in a feeder free environment.

In another embodiment, the desired cell is any cell that is supposed to be applied to an organ or a part of a subject in need thereof. The desired cell is, for example, a cell applied to a heart, lung, liver, pancreas, kidney, large intestine, small intestine, spinal cord, central nervous system, bone, eye, skin, blood vessel or blood.

In another embodiment, the desired cells are, by way of non-limiting example, mesenchymal stem cells, skeletal myoblasts, pluripotent cardiac progenitor cells, unipotent cardiac progenitor cells, or cardiomyocytes, skeletal muscle cells, smooth muscle cells, hemangioblasts, epithelial cells, endothelial cells, lung cells, liver cells, pancreatic cells, renal cells, adrenal cells, intestinal epithelial cells, neural stem cells, bone marrow stromal cells, neural cells, corneal epithelial cells, corneal endothelial cells, retinal pigment epithelial cells, T cells, NK cells, NKT cells, dendritic cells, or blood cells. The desired cell may also be a cell derived from an iPS cell into which any useful gene other than a gene for reprogramming has been introduced, for example, a T cell derived from an iPS cell into which a gene of chimeric antigen receptor described in Themeli M. et al. Nature Biotechnology, vol. 31, no. 10, pp. 928-933, 2013 has been introduced. Moreover, gene transfer may be performed on the desired cells in the cell culture obtained by the method of the present disclosure.

In another embodiment, cells obtained by inducing differentiation from pluripotent stem cells include one kind of liver parenchymal cells, sinusoidal endothelial cells, Kupffer cells, stellate cells, pit cells, biliary epithelial cells, vascular endothelial cells, vascular endothelial precursor cells, fibroblasts, bone marrow-derived cells, fat-derived cells, mesenchymal stem cells, or a mixture of two or more kinds of these cells.

In another embodiment, for the purpose of regeneration of kidney tissue, preparation of artificial kidney simulating kidney tissue, or a method for evaluating kidney function, for example, cells obtained by inducing differentiation from pluripotent stem cells include one kind of kidney cells, granule cells, collecting ductal epithelial cells, parietal epithelial cells, foot cells, mesangial cells, smooth muscle cells, tubular cells, interstitial cells, glomerular cells, vascular endothelial cells, vascular endothelial precursor cells, fibroblasts, bone marrow-derived cells, fat-derived cells, mesenchymal stem cells, or a mixture of two or more kinds of these cells.

In another embodiment, for the purpose of regeneration of adrenal tissue, preparation of artificial adrenal gland simulating adrenal gland, or a method for evaluating adrenal function, for example, cells obtained by inducing differentiation from pluripotent stem cells include one kind of adrenal medulla cells, adrenocortical cells, spherical layer cells, fasciculata cells, reticuloepithelial cells, vascular endothelial cells, vascular endothelial precursor cells, fibroblasts, bone marrow-derived cells, fat-derived cells, mesenchymal stem cells, or a mixture of two or more kinds of these cells.

In another embodiment, for the purpose of regeneration of skin or a method for evaluating skin function, for example, cells obtained by inducing differentiation from pluripotent stem cells include one kind of epidermal keratinocytes, melanocytes, hair growth muscles, hair follicle cells, vascular endothelial cells, vascular endothelial precursor cells, fibroblasts, bone marrow-derived cells, fat-derived cells, and mesenchymal stem cells, or a mixture of two or more kinds of these cells.

In another embodiment, for the purpose of regeneration of mucosal tissue or a method for evaluating mucosal tissue function, for example, cells obtained by inducing differentiation from pluripotent stem cells include one kind of buccal mucosa, gastric mucosa, intestinal mucosa, olfactory epithelium, oral mucosa, and uterine mucosa, or a mixture of two or more kinds of these cells.

In another embodiment, for the purpose of regeneration of nervous system or obtaining a cell for evaluating nerve function, for example, cells obtained by inducing differentiation from pluripotent stem cells include one kind of midbrain dopamine neurons, cerebral neurons, retinal cells, cerebellum cells, and hypothalamic endocrine cells, or a mixture of two or more kinds of these cells, but are not particularly limited thereto.

In another embodiment, when it is intended to obtain cells that constitute blood, for example, cells obtained by inducing differentiation from pluripotent stem cells include one kind of T cells, B cells, neutrophils, eosinophils, basophils, monocytes, platelets, red blood cells, or a mixture of two or more kinds of these cells, but are not particularly limited thereto.

In another embodiment, cell cultures, compositions and the like containing the desired cells of the present invention are for treating a disease. In addition, the culture containing the desired cells of the present invention may be used for producing a composition for treating a disease and the like. Diseases include, for example, heart disease, lung disease, liver disease, pancreas disease, kidney disease, large intestine disease, small intestine disease, spinal cord disease, central nervous system disease, bone disease, eye disease or skin disease, etc., but are not particularly limited thereto. If the desired cell is a cardiomyocyte, diseases include heart disease with myocardial infarction (including chronic heart failure associated with myocardial infarction), dilated cardiomyopathy, ischemic cardiomyopathy, or systolic dysfunction (e.g., left ventricular systolic dysfunction) (e.g., heart failure, especially chronic heart failure) and the like. The disease may be treated with desired cells and/or a sheet-shaped cell culture (cell sheet) of the desired cells, which is useful for the treatment.

One aspect is a method for producing a sheet-shaped cell culture, including sheet-forming the cell culture obtained by the method of the present disclosure. The cell culture obtained by this method is optionally frozen and thawed and then is sheet-formed, for example, as described in International Application Publication No. 2017/010544. The method may further include the step of optionally purifying the desired cells before sheet-forming the cell culture.

As a method of purifying the desired cells, various separation methods using markers specific to the desired cells (e.g., cell surface markers, etc.) are included, such as magnetic cell separation (MACS), flow cytometry, an affinity separation method, a method of allowing a selection marker (e.g., an antibiotic resistance gene, etc.) to express with a specific promoter, a method utilizing the auxotrophy of the desired cells, i.e., a method of culturing in a medium from which nutrient sources necessary for survival of cells other than the desired cells is removed to eliminate cells other than the desired cells, a method of selecting a cell capable of surviving under poor nutrition conditions, and a method of collecting the desired cells using a difference in affinity binding to adhesion proteins coated on the substrates between the desired cells and cells other than the desired cells as well as a combination of these methods.

As a method for purifying pluripotent stem cell-derived cardiomyocytes, various separation methods using markers specific to cardiomyocytes (e.g., cell surface markers, etc.) are included, such as magnetic cell separation (MACS), flow cytometry, an affinity separation method, a method of allowing a selection marker (e.g., antibiotic resistance gene, etc.) to express with a specific promoter, a method utilizing auxotrophy of cardiomyocytes, i.e., a method of culturing in a medium from which nutrient sources necessary for survival of cells other than cardiomyocytes is removed to eliminate cells other than cardiomyocytes (Japanese Patent Application No. 2013-143968), a method of selecting cells that can survive under poor nutrition conditions (International Application Publication No. 2007/088874), a method of collecting cardiomyocytes using a difference in affinity binding to adhesion proteins coated on the substrates between the cardiomyocytes and cells other than cardiomyocytes (Japanese Patent Application No. 2014-188180), as well as a combination of these methods may be mentioned (for example, see Burridge et al., Cell Stem Cell. 2012 Jan. 6; 10(1): 16-28). Cell surface markers specific for cardiomyocytes include, for example, CD172a, KDR, PDGFRA, EMILIN2, VCAM and the like. Moreover, a promoter specific for cardiomyocytes includes, for example, NKX2-5, MYH6, MLC2V, ISL1, etc. In one embodiment, cardiomyocytes are purified based on the cell surface marker CD172a.

Another aspect is a kit including a cell population containing the desired cells derived from pluripotent stem cells obtained by the previously described method, a cell culture solution and a culture substrate, and the kit may be hereinafter referred to as "the kit".

One aspect of the kit further includes a medical adhesive and a cell wash solution. The medical adhesive is not particularly limited as long as it is an adhesive used for surgery and the like. Examples of medical adhesives include cyanoacrylate adhesives, gelatin-aldehyde adhesives and fibrin glue adhesives, and fibrin glue adhesives such as Beriplast® (CSL Behring K.K.) and Bolheal® (TEIJIN PHARMA LIMITED.) is preferred. The cell wash solution is a cell wash solution used in the step of washing the cells described above.

The kit may further include desired cells, the above additives, culture dishes, reagents used for purification of cardiomyocytes (e.g., antibody, wash solution, beads, etc.), instruments (e.g., pipette, syringe, tweezers, etc.), and Instructions on how to produce a sheet-shaped cell culture and how to use it (for example, a manual or a medium such as a flexible disk, CD, DVD, Blu-ray disc, memory card, USB memory, etc. recording information on how to produce or how to use the sheet-shaped cell culture).

Another aspect relates to the use of a cell culture, composition or sheet-shaped cell culture containing the desired cells for drug screening. Cell cultures, compositions or sheet-shaped cell cultures containing the desired cells of the present invention may be used as a substitute for animal experimental models conventionally used for drug screening. Those skilled in the art can appropriately select and set the type of drug and the screening method.

Another aspect relates to a method of treating a disease, the method including applying an effective amount of a cell culture, composition, or sheet-shaped cell culture and the like containing the desired cells to a subject in need thereof. The diseases to be treated are as previously described.

In the present disclosure, the term "treatment" is intended to encompass all kinds of medically acceptable prophylactic and/or therapeutic interventions aimed at curing, temporary remission or prevention of diseases. For example, the term "treatment" includes medically acceptable interventions for a variety of purposes, including delaying or halting the progression of a disease associated with tissue abnormalities, regression or disappearance of a lesion, prevention of the onset of the disease, or prevention of recurrence.

In the treatment method, a component that enhances the viability, engraftment and/or function of cell cultures, compositions or sheet-shaped cell cultures, or other active ingredients useful for treating a targeted disease, etc. can be used in combination with the cell culture, composition, sheet-shaped cell culture and the like.

The treatment method may further include the step of producing the sheet-shaped cell culture according to the foregoing production method. The treatment method of the may further include, before the step for producing a sheet-shaped cell culture, a step of collecting cells for producing a sheet-shaped cell culture from a subject (for example, skin cells, blood cells, etc. when using iPS cells) or tissue (e.g., skin tissue, blood, etc. when using iPS cells) from which cells are supplied, may be included. In one embodiment, the subject from whom the cells or tissue from which the cells are supplied is collected is the same individual as the subject receiving administration of the cell culture, the composition, or the sheet-shaped cell culture and the like. In another embodiment, the subject from whom the cells or tissue from which the cells are supplied is a separate entity of the same species as the subject receiving administration of the cell culture, the composition, or the sheet-shaped cell culture and the like. In another embodiment, the subject from whom the cells or tissue from which the cells are supplied is an individual that is heterologous to the subject receiving administration of the cell culture, the composition, or the sheet-shaped cell culture.

In the present disclosure, an effective amount is, for example, an amount (for example, size, weight, number of sheets, etc. of sheet-shaped cell culture) capable of suppressing the onset or recurrence of a disease, reducing symptoms, or delaying or stopping the progression, and preferably, it is an amount that prevents the onset and recurrence of the disease or cures the disease. Also preferred is an amount that does not adversely affect the benefits of administration. Such amount may be determined as appropriate, for example, by tests in experimental animals such as mice, rats, dogs or pigs, or in disease model animals, and such test methods are well known to those skilled in the art. In addition, the size of the tissue lesion to be treated may be an important indicator for determining the effective dose.

Methods of administration include, for example, intravenous administration, intramuscular administration, intraosseous administration, intrathecal administration, direct application to tissues, and the like. Although the frequency of administration is typically once per treatment, multiple administrations may also be performed if the desired effect cannot be obtained. When applied to tissue, the cell culture, composition, sheet-shaped cell culture and the like of the present invention may be fixed to the target tissue by locking means such as sutures or staples.

In one embodiment, treatment of inducing cardiomyocytes from pluripotent stem cells is carried out by sequentially causing (1)a combination of BMP4, bFGF and activin A; (2) a combination of VEGF and IWP-3; and (3) a combination of VEGF and bFGF to act on embryoid bodies formed by the action of BMP4.

In another embodiment, a cell population in which embryoid bodies are dispersed is obtained by treating embryoid bodies obtained by the above treatment of inducing cardiomyocyte with a protease, for example, the above enzyme, preferably TrypLE® Select Enzyme (10×), no phenol red (Thermo Fisher Scientific K.K.) prepared to have a concentration of 3 times higher, etc., dispersing the embryoid bodies into single cells, and removing the remaining cell aggregates with a strainer (BD Biosciences).

In another embodiment, a cell population in which embryoid bodies are dispersed is seeded on a plate coated with gelatin or the like at a density which reaches confluence or higher, and is optionally treated with brentuximab-Vedotin. After an arbitrary number of culture days, cells are recovered to obtain a cell culture containing a high proportion of cardiomyocytes.

In another embodiment, the obtained cell culture is optionally frozen and thawed in any known manner, for example as described in International Application Publication No. 2017/010544 and then sheet-formed.

In another embodiment, the number of viable cells in the obtained cell culture may be measured, for example, by performing trypan blue staining. The number and proportion of cells such as cardiomyocytes and undifferentiated cells may be measured, for example, by flow cytometry or quantitative PCR.

EXAMPLES

Aspects will be described in more detail with reference to the following examples, which illustrate specific non-limiting examples.

Example 1: Method by High Density Culture (1) Maintenance Culture and Differentiation Induction of Human iPS Cells The human iPS cell line for clinical use established by CiRA, Kyoto University was used, and was maintained and cultured by a feeder free method with reference to Nakagawa M. et al., Scientific Reports, 4:3594 (2014). Method of inducing the differentiation was implemented with reference to Miki K. Cell Stem Cell (2015), International Application Publication No. 2014/185358 and International Application Publication No. 2017/038562.

Specifically, human iPS cells maintained and cultured in a culture solution containing no feeder cells were cultured for one day in StemFit® AK03 medium (Ajinomoto Co., Inc.) containing 10 µM Y27632 (Wako Pure Chemical Industries, Ltd.) on EZSPHERE™ (AGC Inc.), the obtained embryoid body was cultured in a culture solution containing activin A, bone morphogenetic protein (BMP) 4, and basic fibroblast growth factor (bFGF), the embryoid body was further cultured in a culture solution containing Wnt inhibitor (IWP3), BMP4 inhibitor (Dorsomorphin) and TGFβ inhibitor (SB431542), followed by culturing in a culture solution containing VEGF and bFGF.

(2) Dispersion of Embryoid Bodies into Single Cells

For embryoid bodies containing cardiomyocytes after induction of differentiation, with using a solution of TrypLE® Select Enzyme (10×), no phenol red (Thermo Fisher Scientific K.K.) with its concentration diluted by three times with 1 mM EDTA, the cells were dispersed into single cells by incubating at 37° C. for ten minutes. Remaining cell aggregates were removed with a strainer (BD Biosciences) and were subject to subsequent experiments.

(3) Seeding and Culturing at High Density

In a medium containing 10% FBS (Moregate, 553-04423) in DMEM High Glucose medium (NACALAI TESQUE, INC., 08458-16) in a gelatin-coated 6-well plate (culture area 9.6 cm$^2$) (hereinafter DMEM-10% FBS medium), 10 µM of Y27632 (ROCK inhibitor) was added, and the dispersed cardiomyocytes were seeded at 1.8×10$^7$. When performing Adcetris® treatment, Adcetris® treatment was performed from the next day, and the treatment was performed at 5 µg/ml for 48 hours. Thereafter, the medium was changed to DMEM-10% FBS medium, and culture was continued for 48 hours.

(4) Evaluation

The number of cells was calculated by performing trypan blue staining, and the cell recovery rate was calculated from the number of viable cells recovered relative to the number of seeded cells. The measurement of cardiomyocyte purity was performed with a flow cytometer after fixing and permeabilizing dispersed cells using BD Cytofix/Cytoperm® Fixation/Permeabilization Solution Kit (BD Biosciences), and then sequentially reacting anti-human troponin antibody (Thermo Fisher Scientific K.K.), and labeled secondary antibody (Thermo Fisher Scientific K.K.). The proportion of the number of cells expressing Lin28 as an undifferentiated cell marker, was determined by quantitative PCR.

(5) Results

The results are shown in FIG. 1. The troponin positive rate of the cell population before seeding was 30%, but in the case where Adcetris® treatment was not performed, after five days of total culture days, the troponin positive rate after seeding was 64%, the number of recovered cells was 7.7× 10$^6$, the cell recovery rate was about 43%, and the positive rate of Lin28, which is an undifferentiated cell marker, was 0.4%.

For those treated with Adcetris®, after five days of total culture days, the troponin positive rate was 62%, the number of recovered cells was 9.9×10$^6$, the recovery rate was about 56%, and the Lin28 positive rate was 0.2%.

The results for other lots carried out in the same manner are shown in Table 1. In all lots, after five days of total culture days, the troponin positive rate was increased compared to the value before seeding.

The present method has shown surprising and unexpected results that cell cultures with increased troponin positive rate can be obtained with high recovery rate.

TABLE 1

| Change in troponin positive rate (%) | | | |
| --- | --- | --- | --- |
| Lot | Before seeding | 4 Days after culture | 5 Days after culture |
| BJ28 | 73.8% | 61% | 76% |
| BJ11 | 81.5% | 78% | 83% |
| BJ13 | 80.4% | 81% | 83% |
| BJ16 | 58.4% | 43% | 73% |

Comparative Example 1: Low Density Culture Method

The following comparative example was implemented by using the cardiomyocytes produced by the differentiation induction method as described in International Application Publication No. 2017/010544.

The human iPS cell line 253G1 was purchased from RIKEN, and used. Myocardial differentiation induction was performed by using a reactor according to the method described in Matsuura K. et al., Biochem Biophys Res Commun, 2012 Aug. 24; 425(2):321-7. Specifically, undifferentiated 253G1 cells were cultured on a mitomycin C-treated MEF by using a Primate ES medium (REPROCELL) supplemented with 5 ng/ml of bFGF as an undifferentiated maintenance medium. The undifferentiated 253G1 cells of ten plates of 10 cm culture dishes were recovered by using a peeling solution (REPROCELL), suspended in 100 mL of mTeSR medium (STEMCELL Technologies Inc.) supplemented with 10 µM of Y27632 (ROCK inhibitor), and then transferred to a vessel, and culture under stirring was started in a bioreactor (ABLE Corporation). One day later, Y27632 was removed from the medium. The medium was replaced with StemPro™-34 (Life Technologies) after one to three days, 0.5 ng/ml of BMP4 was added after three to four days, 10 ng/ml of BMP4, 5 ng/ml of bFGF and 3 ng/ml of activin A were added after four to seven days, 4 µM of IWR-1 was added after seven to nine days, and 5 ng/ml of VEGF and 10 ng/ml of bFGF were added after day 9 while continuing stirring, and cells were recovered after 16 to 18 days. Thus, a cell population (cell mass) containing cardiomyocytes derived from human iPS cells was obtained. After the cell population was dispersed with 0.05% trypsin/EDTA, the remaining cell aggregates were removed with a strainer (BD Biosciences) and it was subjected to subsequent experiments.

The experiment was performed with reference to Park S. et al., Cardiology 2013; 124:139-150. Using a culture solution (Normal Glucose medium) containing 10% of FBS in DMEM-F12, GlutaMAX™ (Gibco, 10565018) or a culture solution (Low Glucose medium) containing 2% of FBS in DMEM, low glucose, GlutaMAX™ Supplement, pyruvate (Gibco, 10567014), $2 \times 10^6$ cells were suspended in a 6 cm dish (culture area: 21.5 cm$^2$) and then were seeded. The medium was changed once in three days of culture. On the 12th day of culture, the cells were recovered, the number of viable cells was measured, and the troponin positive rate and the undifferentiated cell marker Tra-1-60 positive rate were measured by a flow cytometer. The results are shown in FIG. 2. The troponin positive rate before seeding was 66%, but on the 12th day of culture, the troponin positive rate was 41% under both medium conditions. Moreover, the Tra-1-60 positive rate at that time was 0.1% in both culture conditions. Under Normal Glucose medium conditions, the number of recovered cells was $6 \times 10^5$ and the cell recovery was 30%. Under Low Glucose medium conditions, the number of recovered cells was $5.7 \times 10^5$, and the recovery rate was 29%. This method was to reduce troponin positive rate as compared to the value before seeding.

Comparative Example 2: Reaggregation Method/No Glucose Purification Method

The purification methods of cardiomyocytes were reviewed by the comparison based on those described in International Application Publication No. 2017/010544, International Application Publication No. 2007/088874 and Tohyama S. et al., Cell Stem Cell 12, 127-137, Jan. 3, 2013. The iPS cell-derived cardiomyocytes were suspended in Normal Glucose medium, 10 µM of Y27632 (ROCK inhibitor) was added, and cell aggregates were produced by shaking with a rotary shaker. From the next day, the medium was changed to a lactic acid medium in which lactic acid (Wako Pure Chemical Industries, Ltd., 129-02666) was added to DMEM Glucose free medium (Gibco, 11966-025) to be 4 mM, and the suspension culture continued for a total of five days. Meanwhile, on the third day of culture, the medium was changed with the lactic acid medium again. The cells were recovered on the 5th day of culture, the number of viable cells was measured, and the troponin positive rate was measured by a flow cytometer. The results are shown in FIG. 3. Before purification treatment with lactic acid medium, an average troponin positive rate was 26%, and an average of the number of cells was $6.2 \times 10^7$, but the average troponin positive rate became 48%, and the number of recovered cells was $3.0 \times 10^6$ after five days. The cell recovery rate was 5%. Although this method increases the troponin positive rate, it significantly reduces the cell recovery rate.

Comparative Example 3: Method Using MACS

The methods for purifying cardiomyocytes using antibodies were reviewed by comparison based on those described in Dubois, N. C. et al., Nat. Biotechnol. 29, 1011-8 (2011). The iPS cell-derived cardiomyocytes with an average troponin-positive rate of 51% and an average number of cells of $1.4 \times 10^7$ were reacted with CD172-PE (Miltenyi, 130-099-783) at 4° C. for ten minutes, suspended in Anti-PE Beads after washing, and washed after being reacted for 15 minutes at 4° C. The cells were again suspended in the washing solution and passed through a magnetic separation LS-column, the number of recovered cells was measured, and the troponin positive rate was measured by flow cytometry. The results are shown in FIG. 4. The number of recovered cells was $2.2 \times 10^6$ on average, the troponin positive rate was 92% on average, and the cell recovery rate was 16%. Although this method increases the troponin positive rate, it significantly reduces the cell recovery rate.

The various features described herein may be combined in various ways, and the embodiments obtained by such combinations including combinations not specifically described herein are all within the scope of the disclosed embodiments. Those skilled in the art will also appreciate that numerous and various modifications are possible without departing from the spirit of the present invention, and equivalents including such modifications are also included within the scope of the present invention. Accordingly, it should be understood that the embodiments described herein are merely exemplary and are not intended to limit the scope of the present invention.

What is claimed is:

1. A method for producing a cell culture containing cardiomyocytes, the method comprising:
    differentiating induced pluripotent stem cells into embryoid bodies containing a cell population of both cardiomyocytes and undifferentiated cells, and
    seeding the cell population of both cardiomyocytes and undifferentiated cells by dispersing the embryoid bodies onto a culture vessel at a density ranging from $1.0 \times 10^6$ to $1.875 \times 10^6$ cells/cm$^2$ to produce the cell culture.

2. The method according to claim 1, wherein the cell culture contains the cardiomyocytes at a higher proportion in the seeded cell population than in the cell population before the seeding.

3. The method according to claim 1, wherein the undifferentiated cells include a cell group having a higher proliferation rate relative to the cardiomyocytes, the cell group being different than the cardiomyocytes and being at a lower concentration in the seeded cell population than in the cell population before the seeding.

4. The method according to claim 1, further comprising removing cells having tumorigenicity from the cell population before or after the seeding.

5. The method according to claim 4, wherein the removing of cells having tumorigenicity comprises treating the cell population with Brentuximab-Vedotin before or after the seeding.

6. The method according to claim 1, wherein the induced pluripotent stem cells are human cells.

7. The method according to claim 1, wherein the cell culture possesses a troponin positive rate of 50% to 90% after the seeding.

8. The method according to claim 1, wherein the cell culture possesses a Lin28 positive rate of 0.30% or less after the seeding.

9. A method for producing a sheet-shaped cell culture, the method comprising sheet-forming the cell culture obtained by the method according to claim 1.

10. A method for treating a disease in a subject, the method comprising:
differentiating induced pluripotent stem cells into embryoid bodies containing a cell population of both cardiomyocytes and undifferentiated cells,
seeding the cell population of both cardiomyocytes and undifferentiated cells by dispersing the embryoid bodies onto a culture vessel at a density ranging from $1.0 \times 10^6$ to $1.875 \times 10^6$ cells/cm$^2$;
obtaining a cell culture enriched in the cardiomyocytes; and
applying the cell culture enriched in the cardiomyocytes to the subject.

11. The method according to claim 10, wherein the applying of the cell culture enriched in the cardiomyocytes includes applying the cell culture enriched in the cardiomyocytes to a heart, a lung, a liver, a pancreas, a kidney, a large intestine, a small intestine, a spinal cord, a central nervous system, a bone, an eye, skin, a blood vessel or blood.

12. A method for increasing a proportion of cardiomyocytes in a cell culture, the method comprising:
seeding embryoid bodies, differentiated from induced pluripotent stem cells, containing a cell population of cardiomyocytes and a cell group having a higher proliferation rate relative to the cardiomyocytes onto a culture vessel at a density ranging from $1.0 \times 10^6$ to $1.875 \times 10^6$ cells/cm$^2$ to produce the cell culture.

13. The method according to claim 12, wherein the cell culture possesses a troponin positive rate of 50% to 90% after the seeding.

14. The method according to claim 12, wherein the cell culture possesses a Lin28 positive rate of 0.30% or less after the seeding.

* * * * *